United States Patent [19]
Feingold et al.

[11] Patent Number: 5,654,363
[45] Date of Patent: Aug. 5, 1997

[54] BIOCOMPATIBLE OPTICALLY TRANSPARENT POLYMERIC MATERIAL BASED UPON COLLAGEN AND METHOD OF MAKING

[75] Inventors: Vladimir Feingold, Laguna Niguel; Alexei V. Osipov, Laguna Hills, both of Calif.

[73] Assignee: Staar Surgical Company, Inc., Monrovia, Calif.

[21] Appl. No.: 475,578

[22] Filed: Jun. 7, 1995

Related U.S. Application Data

[63] Continuation-in-part of Ser. No. 279,303, Jul. 22, 1994, abandoned.
[51] Int. Cl.$^6$ .................................................. G02B 7/04
[52] U.S. Cl. ................ 525/64; 351/247; 351/160 R; 527/200; 527/201; 527/207; 593/106; 593/108; 593/449; 524/23; 524/704; 525/937; 623/4
[58] Field of Search ............................ 527/200, 201, 527/207; 523/106, 108, 449; 524/23, 704; 525/937, 64; 351/160 R, 247; 623/4

[56] References Cited

U.S. PATENT DOCUMENTS

| | | | |
|---|---|---|---|
| 4,223,984 | 9/1980 | Miyata et al. | 359/160 H |
| 4,388,428 | 6/1983 | Kuzmo et al. | 523/106 |
| 4,452,925 | 6/1984 | Kuzmo et al. | 523/106 |

*Primary Examiner*—James J. Seidleck
*Assistant Examiner*—Duc Truong
*Attorney, Agent, or Firm*—Klima & Hopkins, P.C.

[57] ABSTRACT

The present invention is biocompatible polymer containing the copolymerization product of a mixture of hydrophobic and hydrophilic acrylic and/or allelic monomers, graft-polymerized with telo-collagen. The present material is useful in the production of deformable lenses, for example, intraocular lenses, refractive intraocular contact lenses, and standard contact lenses useful, for example, for correcting aphekia, myopia and hypermetropia.

6 Claims, No Drawings

BIOCOMPATIBLE OPTICALLY TRANSPARENT POLYMERIC MATERIAL BASED UPON COLLAGEN AND METHOD OF MAKING

RELATED APPLICATION

This application is a continuation in part application of U.S. patent application Ser. No. 08/279,303, filed Jul. 22, 1994, now abandoned which application is incorporated by reference in its entirety.

FIELD OF THE INVENTION

This invention relates to a biocompatible polymer containing the copolymerization product of a mixture of hydrophobic and hydrophilic acrylic and/or allelic monomers, and telo-collagen preliminarily purified from glucoproteins and proteoglucanes. The material is useful for the production of soft intraocular lenses, refractive intraocular contact lenses, and standard contact lenses useful for example, in correcting aphekia, myopia and hypermetropia.

BACKGROUND OF THE INVENTION

Ordinary polymers, based upon pure non-polyenic acrylates or allelic monomers, do not have on their surfaces water-solvent ionic layers on their surfaces which are buffered against the sorption of proteins. Providing water-solvent ionic layers on the surface of the polymer is desirable because such layers will greatly improve the biocompatibility of the lens with cell membranes of the recipient's eye.

Polyenic water-solvent ionic monomers may be used in order to produce a water-solvent layer. However, this decreases the resistance of such copolymers against swelling. For example, the system of polyenic copolymers, based upon acrylamid or acrylic acid with HEMA has a tendency towards excessive swelling beyond all bounds. This happens because pure homopolymers, polyacrylamide or polyacrylic acid, contained in this system, dissolve in water. Therefore, it is an advantage to produce a polymer which would be able to form such a vital water-solvent layer, and would not affect the polymer resistance against swelling.

References concerning graft-copolymers of collagen include U.S. Pat. No. 4,388,428 (Jun. 14, 1983) and U.S. Pat. No. 4,452,925 (Jun. 5, 1994). In these patents, a system of water-soluble monomers and A telo-collagen is used. However, this system is not hydrolytically stable and is not sufficiently optically transparent. In U.S. Pat. No. 4,452,925, nothing is mentioned of special optical conditions needed for transparent polymer production. The water-solvent A telo-collagen disclosed in this patent does not have the capacity to form a gel in the organic monomer solution, and therefore the collagen precipitates or coagulates.

SUMMARY OF THE INVENTION

An object of the present invention is to provide a biocompatible optically transparent polymeric material based on telo-collagen.

A further object of the present invention is to provide a biocompatible polymer containing the copolymerization product of a mixture of hydrophobic and hydrophilic acrylic and/or allelic type-monomers and telo-collagen.

An object of the present invention is to provide a method of making a biocompatible, optically transparent, polymeric material based on collagen.

A further object of the present invention is to provide a method of making a biocompatible polymer containing the copolymerization product of a mixture of hydrophobic and hydrophilic acrylic and/or allelic type-monomers and telo-collagen.

The present invention is directed to methods of making a biocompatible polymeric material based on collagen for use in the production of deformable lenses.

The present invention is also directed to an deformable lens comprised of the present optically transparent, biocompatible, polymeric material.

The present invention is further directed to methods for making deformable lenses.

The present invention is also directed to methods for correcting aphekia (absence of the lens of the eye), myopia or hypermetropia in a patient by surgically implanting in the eye of the patient, the present deformable lens.

The biocompatible polymeric material according to the present invention is made as a copolymerization product of a mixture of hydrophobic and hydrophilic acrylic and/or allelic monomers graft polymerized with telo-collagen. For example, one or more hydrophobic acrylic and/or allelic monomers are mixed with one or more hydrophilic acrylic and/or allelic monomers, and the resultant solution is then mixed with telo-collagen dissolved in one or more hydrophilic acrylic and/or allelic monomers. The resulting material is then irradiated to form the present biocompatible optically transparent polymeric material.

The telo-collagen used in the present invention is essentially type IV collagen obtained from pig's eye sclera or cornea. The collagen is a naturally stable polyenic, which comprises hydrophobic, hydroxylic and polarized amino-acids (Matsumura, T., Relationship Between Amino-Acid Composition and Differentiation of Collagen, *Lut. J. Biochem.* 3(15):265–274 (1972), and Traub W., and Piez K. A., The Chemistry and Structure of Collagen, *Advances in Protein Chem* 25:243–352, (1971). It is not advisable to use a modified collagen in the system according to the present invention since this collagen biodegrades with time (U.S. Pat. No. 4,978,352, Dec. 18, 1990).

The resulting biocompatible polymeric material is an elastic biopolymer, based upon the mixture of the hydrophobic and hydrophilic monomers and telo-collagen. The product of the hydrophobic and hydrophilic monomer copolymerization exhibits an elevated hydrolytic stability and a much higher index of refraction, if compared with a polymer which is based upon hydrophilic monomers alone.

The high molecular mass of telo-collagen molecules (320,000D), their size (up to 1000A), the disorientation of molecules in space, the refraction index 1.47 (Hogan J. J. et. al., *Histology of Human Eyes, An Atlas and Textbook*, Philadelphia, London, Toronto, (1971)), and other characteristics of collagen make it impossible to produce optically transparent hydrogel implants made of collagen alone. The refraction index of the hydrogel base substance, the aqueous number is equal to 1.336, which is substantially different from the refractive index of collagen 1.47, resulting in opacification of the gel, if a suspension of collagen in aqueous monomer is made.

In order to produce an optically homogeneous gel in the mixture of organic monomers it is necessary to utilize telo-collagen containing telo-peptide. Telo-peptide is the basic element of interaction among collagen molecules. This produces a stable gel in the mixture of hydrophobic and hydrophilic monomers, and this gel neither precipitates nor coagulates.

For the purpose of increasing the optical transparency and homogeneity in this system, the refraction index of polymer and of telo-collagen should be approximately equal, so that the intensity of light diffusion is close to zero, in accordance with Reley's equation (U. G. Frolof, *Course of Colidle Chemistry*, Moskva Chemia, 1989):

$$\text{WHEREAS}, I = I_o \left( 24\pi^3 \left( \frac{N_l^2 - N_o^2}{N_l^2 + 2N_o^2} \right) \cdot \frac{C \cdot V^2}{\lambda^4 P_r} (1 + \cos^2 w) \right)$$

$I_o$=is intensity of incident light;
I=is the intensity of diffused light as a unit of radiation volume;
$P_r$=distance to detector;
w=light diffusion angle;
C=concentration of particles per volume unit;
λ=length of incident light wave;
$N_l$=refraction index of particles;
$N_o$=refraction index of basal substance; and
V=volume of particles.

If $N_l = N_o$, then $I_p = 0$. Thus, the intensity of light diffusion is zero.

A preferred hydrophilic acrylic monomer for use in the present invention is 2-hydroxyethyl methacrylate (HEMA), and a preferred hydrophobic monomer for use in the present invention is 4-metharyloxy-2-hydroxybenzophenone. The telo-collagen is preferably produced from pig's eye sclera or cornea.

DETAILED DESCRIPTION OF THE PREFERRED EMBODIMENTS

I. Definitions:

The below definitions serve to provide a clear and consistent understanding of the specification and claims, including the scope to be given such terms.

Telo-collagen. By the term "telo-collagen" is intended for the purposes of this invention a naturally stable polyenic, that contains hydrophobic, hydroxylic and polarized aminoacids (Matsumura, T., Relationship Between Amino-Acid Composition and Differentiation of Collagen *Lut. J. Biochem* 3(15):265–274 (1972).

The present telo-collagen is essentially type IV telo-collagen preferably made from pig's eye sclera or cornea, and has a viscosity of greater than or equal to 1000 cPs. The present telo-collagen retains the telo-peptides and has a refractive index of about 1.44 to 1.48.

Biocompatible polymeric material. By the terminology "biocompatible polymeric material" is intended a material which is made by combining or mixing one or more hydrophobic monomers (acrylic and/or allelic monomers), and one or more hydrophilic monomers (acrylic and/or allelic monomers), and graft-copolymerizing the resultant mixture with a telo-collagen/hydrophilic monomer/acid solution.

Monomer. By the term "monomer" denotes the molecular unit that by repetition, constitutes a large structure or polymer. For example ethylene $CH_2=CH_2$ is the monomer of polyethylene, $H(CH_2)NH$.

Allyl. By the term "allyl" is intended 2-propenyl, the monovalent radical, $CH_2=CHCH_2-$.

Organic Acid. By the term "organic acid" is intended an acid made up of molecules containing organic radicals. Such acids include for example, formic acid (H—COOH), acetic acid ($CH_3COOH$) and citric acid ($C_6H_8O_7$), all of which contain the ionizable —COOH group.

Acrylic. By the term "acrylic" is intended synthetic plastic resins derived from acrylic acids.

Optically Transparent. By the terminology "optically transparent" is intended the property of a polymeric material to allow the passage of light at or above the threshold of visual sensation (i.e., the minimum amount of light intensity invoking a visual sensation). Preferably, the present biocompatible polymeric material including COLLAMER has a refractive index in the range of 1.44 to 1.48, more preferably 1.45 to 1.47, and most preferably 1.45 to 1.46. The best mode of the present invention is the biocompatible polymeric material COLLAMER.

Polymerization. By the term "polymerization" is intended a process in which monomers combine to form polymers. Such polymerization can include "addition polymerization" where monomers combine and no other products are produced, and "condensation polymerization" where a by-product (e.g. water) is also formed. Known suitable polymerization processes can be readily selected and employed for the production of the present biocompatible polymeric material by those of ordinary skill in the art to which the present invention pertains.

Polyene. By the term "polyene" is intended a chemical compound having a series of conjugated (alternating) double bonds, e.g., the carotenoids.

Refractive Index. By the terminology "refractive index" is intended a measurement of the degree of refraction in translucent/transparent substances, especially the ocular media. The "refractive index" is measured as the relative velocity of light in another medium (such as the present polymeric material) as compared to the velocity of light in air. For example, in the case of air to crown glass the refractive index(n) is 1.52, in the case of air to water n=1.33.

Tensile Strength. By the terminology "tensile strength" is intended the maximal stress or load that a material is capable of sustaining expressed in kPa. The present biocompatible polymeric material including COLLAMER has a tensile strength in the range of about 391–1778 kPa, preferably 591–1578 kPa, more preferably 791–1378 kPa, and most preferably in the range of from 991 kPa to 1178 kPa. The present material "COLLAMER" has a tensile strength of preferably 1085±493 kPa. The tensile strength of a polymeric material can be readily determined using known methods, by those of ordinary skill in the art.

Hypermetropia. By the term "hypermetropia" (h.) is intended farsightedness/longsightedness, i.e., long or far sight which is an optical condition in which only convergent rays can be brought to focus on the retina. Such conditions include: (1) absolute h.—that cannot be overcome by an effort of accommodation; (2) axial h.—h. that is due to shortening of the anteroposterior diameter of the globe of the eye; (3) curvature h.—h. which is due to the decreased refraction of the anterior diameter of the globe of the eye; (4) manifest.—h. that can be compensated by accommodation; (5) facultative h.—manifest h.; (6) latent h.—the difference between total and manifest h.; and (7) total h.—that which can be determined after complete paralysis of accommodation by means of a cycloplegic; (8) index h.—h. arising from decreased refractivity of the lens.

Myopia. By the term "myopia" (m) is intended "shortsightedness; nearsightedness; near or short sight; that optical condition in which only rays a finite distance from the eye focus on the retina. Such conditions include: (1) axial m.—m. due to elongation of the globe of the eye; (2) curvature.—m. due to refractive errors resulting from excessive corneal curvature; (3) degenerative.—pathologic m.; (4) index m.—m. arising from increased refractivity of the lens, as in nuclear sclerosis; (5) malignant.—pathologic m.; (6) night.—m. occurring in a normally emmetropic eye because long light rays focus in front of the retina; (7)

pathologic.—degenerative or malignant., progressive. marked by fundus changes, posterior staphyloma and subnormal corrected acuity; (8) prematurity m.,.—m. observed in infants of low birth weight or in association with retrolental fibroplasia; (9) senile lenticular.—second sight; (10) simple m.—m. arising from failure of correlation of the refractive power of the anterior segment and the length of the eyeball; (11) space.—a type of m. arising when no contour is imaged on the retina; and (12) transient.—m. observed in accommodative spasm secondary to iridocyclitis or ocular contusion.

Hydrophilic allelic monomer. By the term "hydrophilic allelic monomer" is intended for the purposes of the present invention any monomer containing an allyl group which monomer is soluble in water.

Hydrophilic acrylic monomer. By the terminology "hydrophilic acrylic monomer" is intended any monomer containing an acrylic group which monomer is soluble in water. For example, HEMA is a hydrophilic acrylic monomer because it is soluble in water even though it contains both hydrophilic groups and hydrophobic groups.

Hydrophobic allelic monomer. By the term "hydrophobic allelic monomer" is intended for the purposes of the present invention, any monomer containing an allyl group, which monomer is not soluble in water.

Hydrophobic acrylic monomer. By the term "hydrophobic acrylic monomer" is intended for the purposes of the present invention, any monomer containing an acrylic group, which monomer is not soluble in water.

Deformable lens. By the term "deformable lens" is intended any type of deformable lens, for example, for correcting hypermetropia or myopia, where the lens comprises the present material. Such lenses include those disclosed in U.S. patent application Ser. Nos. 08/318,991 and 08/225,060. All of the foregoing are hereby incorporated by reference herein. Such lenses include: intraocular lenses for implantation into a patient's eye, for example, into the anterior chamber, in the bag or in the sulcas; refractive intraocular lenses for implantation into a patient's eye, for example, into the anterior chamber or in the sulcas; and standard soft contact lenses.

Implant. By the term "implant" is intended the surgical method of introducing the present lens into the eye of a patient, for example, into the anterior chamber, in the bag or in the sulcas, by the methods described in U.S. patent application Ser. Nos. 08/195,717, 08/318,991, and 08/220,999 using for example, surgical devices disclosed in U.S. patent application Ser. Nos. 08/197,604, 08/196,855, 08/345,360, and 08/221,013. All of the foregoing are hereby incorporated by reference.

The present hydrophilic monomers and hydrophobic monomers must be selected such that the hydrophobic monomer(s) is soluble in the hydrophilic monomer(s). The hydrophilic monomer acts as a solvent for the hydrophobic monomer. Suitable monomers can be readily selected by those of ordinary skill in the art to which the present invention pertains.

Examples of suitable hydrophobic monomers, include:
1) 4-methacryloxy-2-hydroxybenzophenone (acrylic);
2) ethyl-3 benzoil acrylate (acrylic);
3) 3-allyl-4-hydroxyacetophenone (allelic);
4) 2-(2'-hydroxy-3'-allyl-5'-methylphenyl)-2H-benzotriazole (allelic);
5) N-propyl methacrylate (acrylic);
6) allyl benzene (allelic);
7) allyl butyrate (allelic);
8) allylanisole (allelic);
9) N-propyl methacrylate (acrylic);
10) ethyl-methacrylate (acrylic);
11) methyl methacrylate (acrylic);
12) n-heptyl methacrylate (acrylic).

Various examples of suitable hydrophilic monomers, include:
1) 2-hydroxyethyl methacrylate (HEMA) (acrylic);
2) hydroxypropyl methacrylate (acrylic);
3) 2-hydroxyethyl methacrylate (acrylic);
4) hydroxypropyl methacrylate (acrylic);
5) allyl alcohol (allelic);
6) poly(ethylene glycogen monomethacrylate (acrylic);
7) 4-hydroxybutyl methacrylate (acrylic);
8) allyl glucol carbonate (allelic).

II Method of Making the Present Polymeric Material Based on Collagen

The following is a description of a preferred method of making the biocompatible polymeric material according to the present invention.

Step 1:

The hydrophilic monomer is mixed with an acid, in particular formic acid. The weight ratio of hydrophilic monomer to acid is preferably in the range of about 5:1 to about 50:1, preferably 14:1 to 20:1, and most preferably, 14:1. This solution is preferably filtered through a 0.2 microfilter.

Step 2:

In an independent step, an acidic telo-collagen solution is prepared by mixing telo-collagen with organic acid (preferably formic acid). The solution is preferably 2% by weight telo-collagen in 1M formic acid.

Step 3:

The solutions resulting from steps 1 and 2 are then mixed together. The resultant solution is preferably mixed from about 10 minutes to 60 minutes, most preferably 20 minutes at a temperature of 15°–30° C. The ratio of telo-collagen to hydrophilic monomer is about 1:2 to about 1:7, preferably 1:3 to 1:6, and most preferably 1:4.

Step 4:

In an independent step, the hydrophobic monomer and hydrophilic monomer are mixed together in a weight ratio of about 10:1 to 1:1, preferably 8:1 to 3:1, and most preferably 5:1. The monomers are mixed with stirring for about 30 to 90 minutes, preferably 60 minutes at 70° to 95° C., preferably 80°–95° C., and most preferably 80°–92° C. The resulting solution is preferably filtered through a 0.2 micron filter.

Step 5:

The solutions from steps 3 and 4 are mixed together in a weight ratio in the range of about 1:1 to 50:1, preferably 2:1 to 5:1, and most preferably 3:1. The solution is preferably mixed 20 minutes with no heating at a temperature of 25°–40° C. Mixing is preferably performed with a homogenizer.

Step 6:

The resulting material from Step 5 is then preferably degassed (i.e., using centrifugation or other means well-known to those of ordinary skill in the art to which the present invention applies).

Step 7:

The resulting material from Step 6 is irradiated to form a final product that can be dried, and stored, (i.e., stored in a desiccator due to its hydroscopic nature). The material from Step 6 can also be stored in a refrigerator, for example at 5° C. to 10° C., prior to irradiation.

A polymeric material according to the present invention is obtained from an interaction between a solution of telo-collagen complex, and the hydrophilic and the hydrophobic monomers under radiation of 1 Mrad/hr for a total dose of from 0.20 to 0.80 Mrad, preferably 0.30 to 0.60 Mrad, and most preferably from 0.35 to 0.50 Mrad (1 Mrad=10 Kgray).

A turbo-type mixer such as a homogenizer, is preferably employed for mixing the solutions of at least Steps 3 and 5, and the mixing times set forth above are based on using a turbo-type mixer. Those of ordinary skill in the art can readily select and employ other known mixers and methods, as well as time ranges.

In a preferred embodiment the present polymeric material is made by mixing the hydrophobic monomer in two stages to increase the solution viscosity, where in stage one the telo-collagen complex and a mixture of formic acid with 2-hydroxyethyl-methacrylate are used as a stabilizer of ultra-colloidal state solution and in stage two a hydrophobic blend of at least one monomer is introduced into the gel produced.

III. Standardized Method for the Compounding of the present COLLAMER

A. Preparation of Acidic Collagen Solution

A 1M acid solution, preferably 1M formic acid is prepared. The quantity of acid solution required for dissolution of the swollen tissue is calculated using a ratio of swollen collagen tissue: (sclera or cornea) acid solution of about 40:0.5 to 55:2, preferably about 45:1 to about 52:1.5, most preferably about 50:1.

The swollen tissue is then dispensed in a homogenizer for about 10 to 20 minutes, preferably about 15 minutes at 2 to 10 RPM, preferably 4–5 RPM, at room temperature. The produced solution is then filtered through a funnel glass filter with a pore size of 100–150 microns, the filtrate is then filtered through a second funnel glass filter with a pore size of 75–100 microns. The produced homogenic solution is then transferred into a container.

B. Hydrophobic and Hydrophilic Solution Preparation

1. The hydrophilic monomer, preferably HEMA is mixed with the hydrophobic monomer, preferably MHBPH in a weight ratio of about 5:1 and heated for one hour at 80° C. to 92° C. with stirring (e.g., using a stirrer hot plate). The heated solution is then filtered through 5.0 micron filter.

2. HEMA is mixed with an organic acid (preferably formic acid), preferably in a weight ratio of about 14:1. This mixture is added to the collagen solution produced (A) in a weight ratio of HEMA solution:collagen solution of about 1:3, and mixed for about 20 minutes at room temperature. The mixing is preferably performed using a homogenizer at a rate of 6000 RPM.

3. The HEMA MHBPH solution of B.(1) is then mixed in small portions with the HEMA telo-collagen solution of B.(2). The mixing is preferably performed in a homogenizer for 10 minutes at room temperature.

C. Production of COLLAMER

Glass vials are then coated with approximately 7 mm of paraffin wax. The solution of B(3) is then poured into the glass vials and degassed (e.g., centrifuged for 15 minutes to remove air). The vials are subsequently irradiated at 5 Kgray. (Note: prior to irradiation the vials can be stored in a refrigerator, for example at 5° C. to 10° C.)

IV. Guidance for Selecting the Present Monomers

The following equation can be used to aid in the selection of the appropriate concentration of monomer necessary to result in the present polymeric material having an index of refraction in the present desired range (1.44 to 1.48, preferably 1.45 to 1.47, and most preferably 1.45 to 1.46).

The monomer of copolymerization with telo-collagen complex is selected such that:

$N = (K_s \cdot N_a) + (1 - K_s) N_p = N_c \pm 0.02$ $K_s$ = coefficient of swelling
$N_a$ = refractive index of water (1.336)
$N_p$ = refractive index of dry polymer
$N_c$ = refractive index of telo-collagen (about 1.45 to 1.46)

$$\text{where } N_p = A \left( \sum_{i=n}^{i=n} N_i \cdot C_i \right)$$

$N_i$ = refractive index of i-monomer
$C_i$ = concentration of i-monomer
A = coefficient of increase in refractive index due to polymerization
n = number of monomers
i = monomer number The hydrophobic and hydrophilic monomers must be selected such that the hydrophilic monomer is a solvent for the hydrophobic monomer, i.e., the hydrophobic monomer is soluble in the hydrophilic monomer.

The manner and method of carrying out the present invention may be more fully understood by those of skill in the art to which the present invention pertains by reference to the following examples, which examples are not intended in any manner to limit the scope of the present invention or of the claims directed thereto.

EXAMPLES

Example I

Compounding COLLAMER

A. Preparation of acidic collagen solution

Under an exhaust hood, 1 liter of distilled water was measured into a 3 liter glass beaker. 52 grams of formic acid was then added to the beaker and mixed until dissolved. Swollen collagen containing tissue (from pig's eyes) was then added to the acid solution in the below ratios of swollen tissue:acid solution.

| Swollen Tissue | Acid Solution |
|---|---|
| 1. 517.00 grams | 10.21 grams |
| 2. 50.64 grams | 1.00 grams |

The mixture was then stored in a refrigerator at a temperature of 5° C., and was thereafter dispersed in a homogenizer for 15 minutes at 4–5 RPM at room temperature.

The produced solution was then filtered through a funnel glass filter with a pore size of 100–150 microns. Thereafter, the filtrate was filtered through a funnel glass filter with a pore size of 75–100 microns. The final homogenic solution was then transferred into a 250 ml container.

B. MHBPH and HEMA solution preparation 1. 527.4 g of HEMA was mixed with 106.2 g of MHBPH and heated for one hour at 80° C. using a stirrer hot plate. The heated solution was filtered through an Acro 50–5.0 micron filter.

2. 1415.6 g of HEMA was then mixed with 99.4 g of formic acid in a hermetic glass container with a Teflon lid.

100 g portions of the HEMA/acid solution were added into 333 g of telo-collagen solution and mixed for 20 minutes at room temperature. The mixing was performed in a homogenizer at a rate of 6000 RPM.

3. The HEMA/MHBPH solution was then added in small portions to the HEMA telo-collagen solution. The mixing was performed in a homogenizer for 10 minutes at room temperature.

C. Production of COLLAMER

Glass vials were coated with approximately 7 mm of paraffin wax. The resultant solution of Step B(3) was then poured into the glass vials and centrifuged for 15 minutes to remove air. The vials were then irradiated at 5 Kgray to polymerize and cross-link the present material.

Example 2

Preparation of a Biocompatible Polymeric Optically Transparent Material

In this example, pig's eye sclera was used. 300 g of 2-hydroxyethyl methacrylate was mixed with 16 g of formic acid. 50 g of telo-collagen was filtered purified from sclera using alkaline hydrolysis with 200 g NaOH and 200 g of $Na_2SO_4$ in 2.5 liters of water, and filtered through a 100 micron filter. The telo-collagen was mixed with 2-hydroxyethyl methacrylate and the formic acid solution containing 2-hydroxyethyl methacrylate. 20 g of 4-methacryloxy-2-hydroxybenzophenone (MHBPH) dissolved in HEMA was then added. This mixture was radiated with gamma radiation in the range of 3.5–5.0 Kgray to polymerize and cross-link all the components.

Hydrophobic monomers were used in this system to reduce the absorption of water and swelling of the polymerized material when introduced into the aqueous media of the eye. In addition, the hydrophobic monomer was chosen so that the refractive index of the resultant polymer increased to be approximately equal to the refractive index of telo-collagen.

Example 3

The same procedure in Example 2 can be utilized, except the following monomers can be substituted:

1) ethyl-3-benzoilacrylate (hydrophobic acrylic monomer), plus
2) 2-hydroxyethyl methacrylate (HEMA), (hydrophilic acrylic monomer).

Example 4

The same procedure in Example 2 can be utilized, except the following monomers can be substituted:

1) 3-allyl-4-hydroxyacetophenone (hydrophobic allelic monomer), plus
2) 2-hydroxyethyl methacrylate (HEMA), (hydrophilic acrylic monomer).

Example 5

The same procedure in Example 2 can be utilized, except the following monomers can be substituted:

1) 2-(2'-hydroxy-3'-allyl-5'-methylphenyl)-2H-benzotriazole (hydrophobic allelic monomer), plus
2) hydroxypropyl methacrylate, (hydrophilic acrylic monomer).

Example 6

The same procedure in Example 2 can be utilized, except the following monomers can be substituted:

1) methyl methacrylate (hydrophobic acrylic monomer), plus
2) hydroxypropyl methacrylate (hydrophilic acrylic monomer).

Example 7

The same procedure in Example 2 can be utilized, except the following monomers can be substituted:

1) 2-(2'-hydroxy-3'-allyl-5'-methylphenyl)-2H-benzotriazole (hydrophobic allelic monomer), plus
2) hydroxypropyl methacrylate (hydrophilic acrylic monomer).

Example 8

A. Tensile Strength Testing of COLLAMER Material

The purpose of this test was to determine the tensile properties of the present collamer material. This includes tensile strength, Young's modulus, and percent elongation at failure. The data collected was used to construct standards for inspection. The tensile test is similar to the silicone tensile test. The sample geometry is different but the stress fundamentals remain the same.

B. Materials

COLLAMER samples
Instron tensile tester (Model 1122)
forceps
log book

C. Procedure

1. Sample Preparation a. The dry material samples were cut into rings. The dimensions are: Outside diameter=10±0.1 mm, inside diameter=8±0.1 mm, thickness=1.0±0.01 mm. The material was prepared following the procedures used to manufacture lenses. Lenses were hydrated following MSOP #113AG.

2. Testing a. The instron tester was set up for tensile specimens, following ESOP 202, RMX-3 Slab Pull Test, Rev B. The fixtures were placed into the jaws and the fixtures were brought together so that the top and bottom portion touched, by moving the crosshead up or down. When the fixtures were touching, there was approximately 8 mm between the two pins. This was the starting position of jaw separation, so the Instron position coordinates were set to zero.

b. The load dial was set to 2 kg full scale output, the crosshead speed to 500 mm/min and the chart recorder to 500 mm/min. The chart speed corresponded to and recorded jaw separation. The chart buttons marked "PEN" and "TIME" were depressed.

c. The wet test sample was removed from its vial and placed so it was almost stretched between the two pins. When the sample was in place, the "UP" button on the crosshead control panel was immediately pressed. This sample was then loaded to failure.

d. When the sample failed, the "STOP" button on the crosshead control panel was pressed. The chart buttons marked "PEN" and "TIME" were then depressed so that they were in the up position the return on the crosshead control panel was then pressed to return the crosshead to starting position.

e. The failure point in the chart was then marked by noting the load at failure (in kg) and jaw separation.

f. Steps 2a through 2e were repeated until all samples were all tested.

C. Data

Calculation for Ultimate Tensile Strength (1) $\sigma = F/A$

Where:

$\sigma$=Ultimate Tensile Strength, Pascals, (Pa).

F=Force required to break the test specimen, Newtons, (N)

A=Hydrated cross sectional area of specimen, square meters, (m$^2$).

$\delta$=Swell Factor, 1.17 w=width, mm t=thickness, mm

Given:

F=0.29 kg×9.81 m/s$^2$=2.84N

A=2[$\delta$(w)×$\delta$(t)]=2[(1.17×1.0)×(1.17×1.0)]=2.74 mm$^2$

Conversion from mm$^2$ to m$^2$: 2.74 mm$^2$=2.74×10$^{-6}$ m$^2$

A=2.74×10$^{-6}$ m$^2$

Find:

Ultimate Tensile Strength, $\sigma$

Solution:

$\sigma$=F/A=2.84N/2.74×10$^{-6}$ m$^2$=1038.3 kPa

To convert kPa to psi, multiply by 145.04×10$^{-3}$ 1038.3 kPa×145.04×10$^{-3}$=150.6 psi $\sigma$=1038.3 kPa or $\sigma$=150.6 psi Calculation for Percent Elongation (2) $\delta = 200[L/MC_{(TS)}]$ Where:

$\delta$=elongation (specified), percent,

L=increase in jaw separation at specified elongation, (mm), and

MC$_{(TS)}$=mean circumference of test specimen, mm, circumference=$\pi$d

Given:

L=41.5 mm

MC$_{(TS)}$=($\pi$d$_1$+$\pi$d$_2$)/2=($\pi$×10 mm+$\pi$×8 mm)/2=28.27 mm

Find:

Elongation, $\delta$

Solution:

$\delta$=200[L/MC$_{(TS)}$]=200[41.5 mm/28.27 mm]=293.6%

$\delta$=293.6[{]jf44bCalculation for Young's Modulus (3) E=Pl/Ae

Where:

E=Young's Modulus, Pascals, (Pa)

P=Force, Newtons, (N)

L=length of sample, meters (m)

A=Cross Sectional Area, square meters, (m$^2$)

e=Gross Longitudinal Deformation, meters, (m).

Given:

P=0.29 kg×9.81 m/s$^2$=2.84N

L=0.008 m

A=A=2[$\delta$(w)×$\delta$(t)]=2[(1.17×1.0)×(1.17×1.0)]=2.74 mm$^2$

Conversion from mm$^2$ to m$^2$: 2.74 mm$^2$=2.74×10$^{-6}$ m$^2$

A=2.74×10$^{-6}$ m$^2$ e=0.0415 m

Find:

Young's Modulus, E

Solution:

E=Pl/Ae=(2.84N×0.008 m)/(0.0415 m×2.74×10$^{-6}$ m$^2$)=200.2 kPa

To convert kPa to psi, multiply by 145.04×10$^{-3}$ 199.8 kPa×145.04×10$^{-3}$=29.0 psi E=199.8 kPa or 29.0 psi

E. Discussion

The Instron was set up and calibrated according to ESOP #202. The testing fixtures were brought together so the centerlines were aligned and there was approximately 8 mm between the posts. This was designated zero and the fixtures returned to this position every time after the test. Crosshead speed and the chart recorder speed were set to 500 mm/min.

The chart recorder was set at zero load and deflection before every test. The chart recorder recorded kilograms-force load and jaw separation. Load is used to determine the ultimate tensile strength (see formula 1, Test Data Section), the stress at which the sample fails. The sample was not set up to test elongation using a standard gage length but a formula in the ASTM D412 standard is used to calculate the elongation (see formula 2, Data Section).

The performance of the specimen proved the material to be elastic and with the stress increasing at a linear rate until failure. The linear increase can be one of two things: (1) it is possible the specimens have stress risers on the inside diameter. Stress risers would be caused by the milling process, because it doesn't have the surface finish of the lathe-turned outer diameter; this may not allow the material to neck down during the plastic deformation stage of the test. The majority of the stress is concentrated on the internal circumference, which loads the stress risers more than if they were on the outside circumference; (2) the material may not neck down (plastic deformation) as do other plastic materials such as Kapton film. It reacts like RMX-3, with the cross sectional area getting smaller as elongation increases, which is indicative of Hooke's law.

The present material showed COLLAMER good resistance to tear propagation, which would happen at any stress risers. The cross sectional area of the failed part was flat, which was indicative of elastic failure.

E. Conclusion

The combined data from the present COLLAMER samples gave an average tensile strength of 1084.6 kilopascals (kPa), and an average elongation of 324.9 percent (%). The tolerance for average tensile strength was calculated as ±3 times the standard deviation, giving an upper tolerance of 1578 kPa (229 psi) and a lower tolerance of 591 kPa (86 psi). The tolerance for the elongation is calculated in the same manner. The upper tolerance is 395% elongation and the lower tolerance is calculated as 255% elongation. See Appendix 3 for the calculations. The tensile strength standard is 1085±493 kPa (157±71 psi) and the elongation is 325%±70. Young's modulus standard is 189±25 kPa (27±11 psi).

F. References

ASTM D412 Properties of Rubber in Tension

ESOP 202—RMX-3 Slab Pull Test, Rev B.

*Mark's Standard Handbook for Mechanical Engineers*, Ninth Edition

All references cited are hereby incorporated by reference. Now having fully described this invention, it will be understood by those of skill in the art that the scope may be performed within a wide and equivalent range of conditions, parameters, and the like, without affecting the spirit or scope of the invention or of any embodiment thereof.

We claim:

1. A deformable lense comprising a biocompatible, optically transparent, polymeric material based on telo-collagen, said polymeric material based on collagen, comprising:

one or more hydrophilic acrylic or allelic monomers, and one or more hydrophobic acrylic or allelic monomers; and telo-collagen containing telo-peptides, wherein said one or more hydrophilic acrylic or allelic monomers and said one or more hydrophobic acrylic or allelic monomers, are graft-polymerized with said telo-collagen to form a biocompatible, optically transparent, polymeric material based on telo-collagen.

2. The deformable lens of claim 1, wherein said deformable lens is a contact lens.

3. The deformable lens of claim 1, wherein said deformable lens is a soft intraocular lens.

4. The deformable lens of claim 1, wherein said deformable lens is a refractive intraocular lens.

5. The deformable lens of claim 1, wherein said deformable lens has a tensile strength of from about 591 kPa to about 1578 kPa.

6. A deformable lense comprising a biocompatible, optically transparent, polymeric material based on telo-collagen, comprising:

HEMA and MHBPH; and telo-collagen containing telo-peptides, wherein said HEMA and said MHBPH are graft-polymerized with said telo-collagen to form a biocompatible, optically transparent, polymeric material based on telo-collagen.

* * * * *